United States Patent
Verfaillie et al.

(10) Patent No.: US 11,492,596 B2
(45) Date of Patent: Nov. 8, 2022

(54) METHODS FOR DIFFERENTIATING CELLS INTO HEPATIC STELLATE CELLS

(71) Applicants: Katholieke Universiteit Leuven, Leuven (BE); Institut D'Investigacions Biomediques August PI I Sunyer (IDIBAPS), Barcelona (ES)

(72) Inventors: Catherine Verfaillie, Leuven (BE); Ruben Boon, Leuven (BE); Pau Sancho Bru, Barcelona (ES); Mar Col Loperena, Barcelona (ES); Luis Perea Sanchez, Barcelona (ES)

(73) Assignees: Katholieke Universiteit Leuven, Leuven (BE); Institut D'Investigacions Biomediques August PI | Sunyer (IDIBAPS), Barcelona (ES)

( * ) Notice: Subject to any disclaimer, the term of this patent is extended or adjusted under 35 U.S.C. 154(b) by 1168 days.

(21) Appl. No.: 15/780,798

(22) PCT Filed: Dec. 1, 2016

(86) PCT No.: PCT/EP2016/079464
§ 371 (c)(1),
(2) Date: Jun. 1, 2018

(87) PCT Pub. No.: WO2017/093418
PCT Pub. Date: Jun. 8, 2017

(65) Prior Publication Data
US 2020/0248146 A1 Aug. 6, 2020

(30) Foreign Application Priority Data
Dec. 1, 2015 (GB) .................................... 1521179

(51) Int. Cl.
*C12N 5/071* (2010.01)
*G01N 33/50* (2006.01)

(52) U.S. Cl.
CPC ....... *C12N 5/0672* (2013.01); *G01N 33/5014* (2013.01); *C12N 2501/113* (2013.01); *C12N 2501/119* (2013.01); *C12N 2501/155* (2013.01); *C12N 2506/45* (2013.01); *C12N 2513/00* (2013.01)

(58) Field of Classification Search
CPC .................................................. C12N 5/0672
See application file for complete search history.

(56) References Cited

U.S. PATENT DOCUMENTS

| | | | |
|---|---|---|---|
| 2008/0145342 A1 | 6/2008 | Qian et al. | |
| 2011/0135610 A1 | 6/2011 | Reid et al. | |
| 2012/0009672 A1 | 1/2012 | Sancho-Bru et al. | |
| 2012/0115226 A1 | 5/2012 | Stachelsheid et al. | |
| 2015/0307839 A1 | 10/2015 | Kuppers-Munther et al. | |

FOREIGN PATENT DOCUMENTS

| | | | |
|---|---|---|---|
| WO | 2005045012 A1 | 5/2005 | |
| WO | 2005097980 A2 | 10/2005 | |
| WO | 2010049752 A1 | 5/2010 | |
| WO | 2011158125 A2 | 12/2011 | |
| WO | WO-2011158125 A2 * | 12/2011 | ............. C12N 5/067 |
| WO | 2017093418 A1 | 8/2017 | |

OTHER PUBLICATIONS

Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*
Gomez et al. (2010, Theriogenology, vol. 74, pp. 498-515) (Year: 2010).*
Buta et al. (2013, Stem Cell Res., vol. 11, pp. 552-562) (Year: 2013).*
NIH Guidelines, 11 pages, web printout (Year: 2016).*
Brambrink, et al., Sequential Expression of Pluritpotency Markers during Direct Reprogramming of Mouse Somatic Cells, Cell Stem Cell Article, 2008, 151-159, vol. 2, Elsevier, Inc.
Chin et al., Induced Pluripotent Stem Cells and Embryonic Stems Cells are Distinguished by Gene Expression Signatures, Cell Stem Cell, Jul. 2, 2009, 111-123, vol. 5, Elsevier Inc.
Coll et al., Integrative miRNA and Gene Expression Profiling Analysis of Human Quiescent Hepatic Stellate Cells, Scientific Reports, 2015,1-14, Scientific Reports.
Fernandes, et al., Human hepatic stellate cell line (LX-2) exhibits characteristics of bone marrow-derived mesenchymal stem cells, Experimental and Molecular Pathology, 2011, 664-672, vol. 91, Science Direct Elsevier.
Guan, et al., Pluripotency of spermatogonial stem cells from adult mouse testis, Nature Publishing, Apr. 2006, 1199-1203, vol. 440/27, Nature Publishing Group.
Hanna, et al., Direct Reprogramming of Terminally Differentiated Mature B Lymphocytes to Pluripotency; The Whitehead Institute, Apr. 18, 2008, 250-264, Cell 133, Elsevier Inc.
Jaenisch, et al., Stem Cells, the Molecular Circuitry of Pluripotency and Nuclear Reprogramming, Leading Edge Review, Feb. 22, 2018, 567-582, Cell 132, Elsevier Inc.
Kordes, et al., Hepatic Stellate Cells Support Hematopoiesis and are Liver-Resident Mesenchymal Stem Cells, Cellular Physiology and Biochemstry, 2013, 290-304, Karger.

(Continued)

*Primary Examiner* — Peter Paras, Jr.
*Assistant Examiner* — David A Montanari
(74) *Attorney, Agent, or Firm* — Dinsmore & Shohl LLP (57) ABSTRACT

The invention is directed to methods for culturing cells so that the cells are induced to differentiate into cells that express a hepatic stellate phenotype. The invention is also directed to cells produced by the methods of the invention. The cells are useful, among other applications, for treatment of liver deficiencies, liver metabolism studies, and liver toxicity studies, fibrogenic studies, or to support hepatocyte function in co-culture setting.

11 Claims, 5 Drawing Sheets

(56) References Cited

OTHER PUBLICATIONS

Okita, et al., Generation of germline-competent induced pluripotent stem cells, Nature, Jul. 19, 2007, 313-318, vol. 448, Nature Publishing Group.

Park, et al., Hepatic differentiation of human embryonic stem cells on microcarriers, Journal of Biotechnology, 2014, 39-48, vol. 174, Elsevier B.V.

Schwartz, et al., Pluripotent stem cell-derived hepatocyte-like cells, Biotechnical Advances, 2014, 504-513, vol. 32, Elsevier Inc.

Sancho-Bru, et al., Directed differentiation of murine-induced pluripotent stem cells to functional hepatocyte-like cells, Journal of Hepatology, 2011, 98-107, vol. 54, Elsevier.

Taghdouini, et al., Genome-wide analysis of DNA methylation and gene expression patterns in purified, uncultured human liver cells and activated hepatice stellate cells, Oncotarget, 2015,26729-26745, vol. 6, No. 29, Impact Journals.

Takahashi, et al., Induction of Pluripotent Stem Cells from Mouse Embryonic and Adult Fibroblast Cultures by Defined Factors, 2006, 663-676, Cell 126, Elsevier Inc.

Takahashi, et al., Induction of Pluripotent Stem Cells from Adult Human Fibroblasts by Defined Factors, 2007, 861-872, Cell 131 Elsevier Inc.

Wernig, et al., Neurons derived from reprogrammed fibroblasts functionally integrate into the fetal brain and improve symptoms of rates with Parkinson's disease, National Academy of Sciences of the USA, 2008, 5856-5861, vol. 105, PNAS.

Wilmut, et al., Viable offspring derived from fetal and adult mammalian cells, Letters to Nature, 1997, 810-814, vol. 385, Nature Publishing Group.

Yamanaka, Strategies and New Developments in the Gernation of Patent-Specific Pluripotent Stem Cells, Cell Stem Cell Review, 2007, 39-49, Cell Stem Cell 1, Elsevier Inc.

Ying, et al. Changing potency by spontaneous fusion, MacMillan Magazines Ltd., 2002, 545-548, vol. 416, Nature.Com.

International Search Report and Written Opinion pertaining to PCT/EP2016/079464 dated Feb. 1, 2017.

* cited by examiner

A. Pro-fibrogenic response

B. Pro-inflammatory response

Fig. 8

METHODS FOR DIFFERENTIATING CELLS INTO HEPATIC STELLATE CELLS

FIELD OF THE INVENTION

The invention is directed to methods for culturing cells so that the cells are induced to differentiate into cells that express a hepatic stellate cell (HSC) phenotype. The invention is also directed to cells produced by the methods of the present invention. The cells can be used for, amongst other applications, treatment of liver deficiency, liver metabolism studies, and liver toxicity studies.

BACKGROUND OF THE INVENTION

Hepatic stellate cells (HSC) are cells of the liver with a mesenchymal origin. They reside in the space of Disse, lining hepatocytes and endothelial sinusoidal cells. In a healthy liver HSC are responsible for extracellular matrix homeostasis and accumulating vitamin A. Under liver damage conditions they activate and secrete a number of cytokines and growth factors as well as extracellular matrix components, which are crucial for the wound-healing response of the liver.

HSC can be isolated from human and animal liver tissue and cultured in vitro. Activated HSC are the main cell type involved in liver fibrosis, and for this reason, cultured HSC have been extensively used as in vitro model of liver fibrosis and for the analysis of the effects of fibrogenic mediators. However, primary cells are heterogeneous, difficult to obtain and present a limited proliferative capacity. For all this reasons HSC cell lines have been developed and, although do not show all the features of primary cells, are increasingly used for in vitro applications.

Currently there are no methods to direct the differentiation of pluripotent stem cells (PSC) to hepatic stellate cells. In 2011, Sancho-Bru et al. (1) described that during hepatocyte differentiation from PSC, endothelial cells and HSC were co-generated in the culture when following directed endodermal differentiation. In this study however, the generation of HSCs was not directed and could be considered a by-product of the protocol created for the differentiation of hepatocytes. Moreover, following this methodology, Sancho-Bru et al. (1) described the generation of a small percentage of cells expressing markers of HSC, but no characterization was performed. US20120009672 claims a method to produce cells with a hepatic stellate cell phenotype from PSC comprising a four step protocol of about 28 days. The described methodology was developed to generate cells of the endodermal phenotype, and therefore the generation of HSC of the mesenchymal origin is not efficient. The number of cells expressing some markers of HSC are generated in a small percentage of the total population. Following this protocol, only 3%-5% of the cells show a fluorescent phenotype under UV Laser, thus suggesting that it may be a population enriched in HSC.

Although cultures of primary HSC are extensively used for fibrogenic analysis, nowadays, the use of HSC for biotechnological and biomedical applications is not common. The lack of reliable sources and homogeneous cultures of primary HSC prevented its use for broad biotechnological applications, and other cells of mesenchymal origin have been evaluated as replacements of HSCs. Although several protocols have been used to differentiate cells of mesenchymal origin, none of them generate cells with phenotypic and functional characteristics of HSC.

Thus, there is a clear need in the art for a novel method for producing cells with a hepatic stellate phenotype.

SUMMARY OF THE INVENTION

The invention is based on methods developed by the inventors to produce a renewable source of hepatic stellate cells in vitro. The present invention provides a novel method to produce HSC-like cells from PSC which are enriched in PDGFRβ-positive cells, express typical HSC markers and exert HSC functions.

The method of the present invention is directed to generate cells of the mesenchymal origin and is therefore much more efficient than previously described protocols such as the protocol claimed in US20120009672. Following the current protocol, between 50-80% of the cells have a HSC-like phenotype. Moreover, the cells generated have a phenotype similar to primary HSC as further described in the detailed description. The present invention provides a shorter method of about 14 days for producing cells with a hepatic stellate phenotype and has a cost of about 25% of the cost of previously described protocol (US20120009672).

The methods described herein can be carried out with or without serum. This may depend on the species of the pluripotent cell that is being differentiated, such as rodent, human, etc. In one embodiment, the serum is fetal bovine serum. Whether serum is required can be determined empirically.

Any cell can be used in the initial step of culture with BM P4 as long as it has a phenotype of a cell that is prior to the primitive streak. Such a cell could express Oct3/4. For an embryonic stem cell, for example, the phenotype would be inner cell mass cell or epiblast. Cells include, but are not limited to, primordial germ cells, embryonic germ cells, cells produced by somatic cell nuclear transplantation into oocytes, tumor cell lines, embryonal carcinoma cells, blastomere cells, inner cell mass cells, embryonic stem cell cultures and lines, spermatogonial stem cells, epiblast cells, and other non-embryonic stem cells, such as reprogrammed somatic cells (IPSC). In one embodiment, such cells express Oct3/4 at levels greater than about 0.1% of Oct3/4 expression in embryonic stem cells.

Another aspect of the present invention relates to the use of the HSC generated by the methods of the present invention.

The invention is also directed to methods of using the cells produced by the methods for treatment of liver deficiencies.

The invention is also directed to methods of using the cells for studies of liver metabolism, for example, to identify or assess metabolic modulators.

The invention is also directed to methods of using the cells for studies of liver toxicity, for example, to identify or assess the toxicity of specific compounds.

Yet another aspect of the present invention relates to pharmaceutical compositions comprising the HSCs generated by the methods of the present invention. Such compositions are suitable for administration to subjects in need of such cells. The cells would be administered in therapeutically effective amounts.

The hepatic stellate cells may play a role during hepatocyte differentiation and support hepatocyte function in vivo and in vitro. Therefore, these cells may be used adjunctively to hepatocytes in in vivo and in vitro methods, such as treatment of liver deficiencies, assays for liver toxicity, identification of metabolic modulators, etc., as disclosed in this application.

The HSCs can be used in drug discovery methods to screen for agents that are metabolic modulators or otherwise affect the function or phenotype of the cells, such as agents that are toxic to the cells. Such agents include, but are not limited to, small organic molecules, antisense nucleic acids, siRNA, DNA aptamers, peptides, antibodies, non-antibody proteins, cytokines, chemokines, and chemo-attractants. The cells are exposed to the agent and the effect is compared or measured against the normal function/phenotype.

Numbered statements of the invention are as follows:
1. A method for producing cells with a hepatic stellate cell phenotype, comprising:
   (a) culturing pluripotent cells with about 1 ng/ml to about 200 ng/ml BM P4;
   (b) then culturing the cells of step (a) with about 1 ng/ml to about 200 ng/ml FGF1 and about 1 ng/ml to about 200 ng/ml FGF3;
   (c) then culturing the cells of step (b) with about 0.5 μM to about 50 μM retinol and about 10 μM to about 1 mM palmitic acid; and
   (d) isolating hepatic stellate cells produced by the differentiation protocol.
2. The method according to statement 1, wherein the cells are cultured in step (a) with about 20 ng/ml BMP4.
3. The method according to statement 1, wherein the cells are cultured in step (b) with about 20 ng/ml FGF1 and about 20 ng/ml FGF3.
4. The method according to statement 1, wherein the cells are cultured in step (c) with about 5 μM retinol and about 100 μM palmitic acid.
5. The method according to statement 1, comprising:
   (a) culturing pluripotent cells with about 20 ng/ml BMP4;
   (b) then culturing the cells of step (a) with about 20 ng/ml FGF1 and about 20 ng/ml FGF3;
   (c) then culturing the cells of step (b) with about 5 μM retinol and about 100 μM palmitic acid; and
   (d) isolating hepatic stellate cells produced by the differentiation protocol.
6. The method according to any one of the statements 1 to 5, wherein the steps are for at least two days each.
7. The method according to any one of the statements 1 to 5, wherein step (a) is about 4 days, step (b) is about two days, and step (c) is about six days.
8. The method according to any one of the statements 1 to 7, wherein the cells are mammalian.
9. The method according to statement 8, wherein the cells are human, mouse, or rat.
10. The method according to any one of the statements 1 to 9, wherein the cells that are contacted with BMP4 are embryonic stem cells or cells that are not embryonic stem cells, embryonic germ cells or germ cells, and can differentiate into at least one cell type of the group consisting of the endodermal, ectodermal and mesodermal embryonic lineages.
11. The method according to statement 10, wherein the cells are not embryonic stem cells, embryonic germ cells or germ cells, and can differentiate into at least one cell type of the group consisting of the endodermal, ectodermal and mesodermal embryonic lineages.
12. The method according to statement 11, wherein the cells are iPS cells.
13. The method according to statement 11, wherein the cells used in step (a) are isolated from bone marrow, placenta, umbilical cord, muscle, brain, liver spinal cord blood, blood or skin.
14. The method according to any one of the statements 1 to 13, wherein the isolation of HSCs in step (d) is carried out by positive selection for one or both markers selected from the group consisting of p75NTR and PDGFRβ, and/or for UV$^+$.
15. The method according to any one of the statements 1 to 13, wherein the isolation of HSCs in step (d) is carried out by positive selection for the marker PDGFRβ.
16. A pharmaceutical composition comprising the cells produced according to any one of the statements 1 to 15, wherein the cells express at least one of the markers selected from the group consisting of p75NTR, αSMA, COL1α1, DESMIN, PDGFRβ, NCAM, NGF and VIMENTIN.
17. The pharmaceutical composition according to statement 16, wherein the cells express all of the markers DESMIN, PDGFRβ, NCAM, NGF and VIMENTIN.
18. The pharmaceutical composition according to statement 16, wherein the cells express all of the markers p75NTR, αSMA, COL1α1, DESMIN, PDGFRβ, NCAM, NGF and VIMENTIN.
19. The pharmaceutical composition according to any one of the statements 16 to 18, wherein the cells additionally show fluorescence under UV (UV$^+$).
20. The pharmaceutical composition according to any one of the statements 16 to 19 for use in treatment of a subject with a liver deficiency, wherein said treatment comprises administering a therapeutically effective amount of the cells produced according to any one of the statements 1 to 15 to said subject.
21. The pharmaceutical composition for use in treatment according to statement 20, wherein said subject is a human.
22. A screening assay to assess the toxicity of a compound; said assay comprising the steps of:
   (a) producing cells with a hepatic stellate cell phenotype using the method of anyone of statements 1-15;
   (b) incubating said cells with a test compound, and
   (c) determining whether said compound is toxic for said cells

DETAILED DESCRIPTION OF THE INVENTION

Several documents are cited throughout the text of this specification. Each of the documents herein (including any manufacturer's specifications, instructions etc.) are hereby incorporated by reference; however, there is no admission that any document cited is indeed prior art of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only.

The following terms are provided solely to aid in the understanding of the invention.

Definitions

The term "comprising" as used herein, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the (only) relevant components of the device are A and B.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed. For temporal durations such as a certain amount of days, the term "about" is meant to also encompass variations of +/−2 days or less, such as +/−1 day.

The recitation of numerical ranges by endpoints includes all numbers and fractions subsumed within the respective ranges, as well as the recited endpoints.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount".

"Hepatic stellate cells" (HSC) reside in perisinusoidal recesses between adjacent hepatocytes and represent ±8% of the liver. They project long processes (~50 µm) in the space of Disse and between adjacent hepatocytes. In the adult liver, HSC are quiescent, produce small amounts of ECM and store vitamin A in the form of retinyl esters in lipid droplets. HSC secrete many cytokines and virtually all growth factors. Not only do the cells secrete the cytokines, they also respond to them. Under pathological conditions, HSC are activated to become myofibroblast-like cells. They proliferate, acquire contractile properties, lose their capacity to store vitamin A and produce excessive amounts of ECM, causing scar formation. This activation is accompanied by changes in gene and miRNA expression, phenotype and function. If the liver injury is limited, HSC revert to a quiescent state or die by apoptosis. However, after prolonged injury, HSC become resistant to apoptosis and their activated phenotype may not be reversible.

HSC can be isolated from normal livers by taking advantage of their high content of lipid droplets that are rich in vitamin A. These lipid droplets are fluorescent under UV light allowing isolation of quiescent HSC by FACS. Moreover, due to their low density it is also possible to isolate them by gradient centrifugation. HSC isolated from normal livers have a quiescent phenotype showing a limited proliferative capacity in culture. Culture conditions for maintaining the quiescent phenotype for an extensive period of time are not known. After 24-48 hours in culture, the cells acquire most of the phenotypic and functional characteristics of activated HSC in injured liver, although their phenotype is not completely identical. When cultured under activating conditions human HSC can be expanded up to 20 doublings.

"Embryonic Stem Cells (ESC)" are well known in the art and have been prepared from many different mammalian species for many years. Embryonic stem cells are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta. Only the morula's cells are totipotent, able to become all tissues and a placenta.

The term "hepatocyte-like cells" is meant to include cells which have similar functionalities as primary hepatocytes, and in particular show phenotypical features of functional hepatocytes when exposed to hepatogenic growth factors. Said phenotypical features may include expression and nuclear localization of liver-specific transcription factors, expression and polarization of drug transporters, expression of plasma proteins and typical building blocks of hepatic intercellular communication, activity of drug metabolizing enzymes at a level similar to primary hepatocytes. In particular, in the context of the present invention, hepatocyte-like cells are meant to include primary human hepatocytes, HepaRG cells, human embryonic stem cells (hESC) differentiated into hepatocyte-like cells, human induced pluripotent stem cells (hiPSC) differentiated into hepatocyte-like cells such as eg. described in WO2010049752, primary fibroblast transdifferentiated into hepatocyte-like cells, or any hepatocyte-like cell line such as HepG2 or huh7, or Upcyted hepatocytes.

Use of the term "includes" is not intended to be limiting. For example, stating that an inhibitor "includes fragments and variants" does not mean that other forms of the inhibitor are excluded.

"Induced pluripotent stem cells (IPSC or IPS cells)" is a designation that pertains to somatic cells that have been reprogrammed, for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., Cell Stem Cell, 1:39-49 (2007)).

For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., PNAS, 105:5856-5861 (2008); Jaenisch et al., Cell, 132:567-582 (2008); Hanna et al., Cell, 133:250-264 (2008); and Brambrink et al., Cell Stem Cell, 2:151-159 (2008).

IPS cells have many characteristic features of embryonic stem cells. For example, they have the ability to create chimeras with germ line transmission and tetraploid complementation and they can also form teratomas containing various cell types from the three embryonic germ layers. On the other hand, they may not be identical as some reports demonstrate. See, for example, Chin et al., Cell Stem Cell 5:111-123 (2009) showing that induced pluripotent stem cells and embryonic stem cells can be distinguished by gene expression signatures.

The term "isolated" refers to a cell or cells that are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only a specific desired cell, such as a stem or hepatic progenitor cell. Rather, the term "isolated" indicates that the cells are removed from their natural tissue environment and are present at a higher concentration as compared to the normal tissue environment. Accordingly, an "isolated" cell population may further include cell types in addition to stem cells and may include additional tissue components. This also can be expressed in terms of cell doublings, for examples. A cell may have undergone 10, 20, 30, 40 or more doublings in vitro or ex vivo so that it is enriched compared to its original numbers in vivo or in its original tissue environment (e.g., bone marrow, peripheral blood, adipose tissue, etc.).

"Pharmaceutically acceptable carrier" is any pharmaceutically-acceptable medium for the cells used in the present invention. Such a medium may retain isotonicity, cell metabolism, pH, and the like. It is compatible with administration to a subject in vivo, and can be used, therefore, for cell delivery and treatment.

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has dedifferentiated, for example, by nuclear transfer, by fusions with a more primitive stem cell, by introduction of specific transcription factors, or by culture under specific conditions. See, for example, Wilmut et al., Nature, 385: 810-813 (1997); Ying et al., Nature, 416:545-548 (2002); Guan et al., Nature, 440:1199-1203 (2006); Takahashi et al., Cell, 126:663-676 (2006); Okita et al., Nature, 448:313-317 (2007); and Takahashi et al., Cell, 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources such as embryoid bodies (although these can be considered embryonic stem cells in that they are derived from embryonic tissue, although not directly from the inner cell mass).

"Self-renewal" refers to the ability to produce replicate daughter stem cells having differentiation potential that is identical to those from which they arose. A similar term used in this context is "proliferation."

"Subject" means a vertebrate, such as a mammal, such as a human. Mammals include, but are not limited to, humans, dogs, cats, horses, cows and pigs.

The term "therapeutically effective amount" refers to the amount determined to produce any therapeutic response in a mammal. For example, effective amounts of the therapeutic cells or cell-associated agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat", "treating" or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

The methods of the present invention induce cells in culture to progress through the appropriate stages of hepatic development, thus recapitulating hepatic development in vitro and, as a result, give rise to cells having hepatic stellate properties.

DETAILED DESCRIPTION OF THE INVENTION

In a first object the present invention presents a method for producing cells with a hepatic stellate cell phenotype, comprising a sequential addition of hepatic differentiation factors to pluripotent cells, wherein there is a first addition (a) of about 1 ng/ml to about 200 ng/ml BMP4, preferably of about 20 ng/ml BM P4; a second addition (b) of about 1 ng/ml to about 200 ng/ml FGF1, preferably of about 20 ng/ml FGF1, and about 1 ng/ml to about 200 ng/ml FGF3, preferably of about 20 ng/ml FGF3; and a third addition (c) of about 0.5 µM to about 50 µM retinol, preferably of about 5 µM retinol, and about 10 µM to about 1 mM palmitic acid, preferably of about 100 µM palmitic acid.

The concentration of BM P4 that is added to the cells in addition step (a) can range from about 1 ng/ml to about 200 ng/ml. However, the invention also encompasses sub-ranges of concentrations of BM P4. For example, from about 1-10 ng/ml, 10-20 ng/ml, 20-30 ng/ml, 30-50 ng/ml, 50-100 ng/ml, 100-150 ng/ml and 150-200 ng/ml. The preferred concentration of BM P4 that is added to the cells in addition step (a) is about 20 ng/ml.

The concentration of FGF1 that is added to the cells in addition step (b) can range from about 1 ng/ml to about 200 ng/ml. However, the invention also encompasses sub-ranges of concentrations of FGF1. For example, from about 1-10 ng/ml, 10-20 ng/ml, 20-30 ng/ml, 30-50 ng/ml, 50-100 ng/ml, 100-150 ng/ml and 150-200 ng/ml. The preferred concentration of FGF1 that is added to the cells in addition step (a) is about 20 ng/ml.

The concentration of FGF3 that is added to the cells in addition step (b) can range from about 1 ng/ml to about 200 ng/ml. However, the invention also encompasses sub-ranges of concentrations of FGF3. For example, from about 1-10 ng/ml, 10-20 ng/ml, 20-30 ng/ml, 30-50 ng/ml, 50-100 ng/ml, 100-150 ng/ml and 150-200 ng/ml. The preferred concentration of FGF3 that is added to the cells in addition step (a) is about 20 ng/ml.

The concentration of retinol that is added to the cells in addition step (c) can range from about 0.5 µM to about 50 µM. However, the invention also encompasses sub-ranges of concentrations of retinol. For example, from about 0.5-2.5 µM, 2.5-5 µM, 5-7.5 µM, 7.5-10 µM, 10-20 µM, 20-30 µM, 30-40 µM and 40-50 µM. The preferred concentration of retinol that is added to the cells in addition step (c) is about 5 µM.

The concentration of palmitic acid that is added to the cells in addition step (c) can range from about 10 µM to about 1 mM. However, the invention also encompasses sub-ranges of concentrations of palmitic acid. For example, from about 10-50 µM, 50-75 µM, 75-100 µM, 100-125 µM, 125-150 µM, 150-175 µM, 175-200 µM, 200-300 µM, 300-400 µM, 400-500 µM, 500-600 µM, 600-700 µM, 700-800 µM, 800-900 µM and 0.9-1 mM. The preferred concentration of palmitic acid that is added to the cells in addition step (c) is about 100 µM.

In a preferred embodiment said method for producing cells with a hepatic stellate cell phenotype, comprises a sequential addition of hepatic differentiation factors to pluripotent cells, wherein there is a first addition (a) of about 20 ng/ml BMP; a second addition (b) of about 20 ng/ml FGF1 and about 20 ng/ml FGF3; and a third addition (c) of about 5 µM retinol and about 100 µM palmitic acid.

In another preferred embodiment, the hepatic stellate cells (HSCs) produced by said method of the present invention are isolated in a fourth step (d) after the third addition step (c) of said method. In a more preferred embodiment, the isolation of said hepatic stellate cells in step (d) after the third addition step (c) is carried out by positive selection for one or both markers selected from the group consisting of PDGFRβ and p75NTR, and/or for fluorescence under UV light (UV). In another more preferred embodiment, said isolation is carried out by positive selection for PDGFRβ. In another more preferred embodiment, said isolation is carried out by positive selection for p75NTR. In another more preferred embodiment, said isolation is carried out by positive selection for PDGFRβ and for UV$^+$. In another more preferred embodiment, said isolation is carried out by positive selection for p75NTR and for UV$^+$. In another more preferred embodiment, said isolation is carried out by selection for UV$^+$.

In another preferred embodiment, each addition step (a), (b) and (c) of said method of the present invention is continued for at least two days, for example two, three, four, five, six, seven or eight days. In more preferred embodiment, the cells are cultured in the first addition step (a) for about 4 days; in the second addition step (b) for about two days; and in the third addition step (c) for about six days.

Preferably, said pluripotent cells used in the first addition step (a) of said method of the present invention are mammalian cells. Preferably, said mammalian cells are human, mouse or rat cells.

In another embodiment, said pluripotent cells are embryonic stem cells or cells that are not embryonic stem cells, embryonic germ cells or germ cells, and can differentiate into at least one cell type of the group consisting of the endodermal, ectodermal and mesodermal embryonic lineages.

In yet another embodiment, the cells are not embryonic stem cells, embryonic germ cells or germ cells, and can differentiate into at least one cell type of the group consisting of the endodermal, ectodermal and mesodermal embryonic lineages. In a preferred embodiment, said cells are induced pluripotent stem cells.

Typically, said cells used in the first addition step (a) of said method of the present invention are isolated from bone marrow, placenta, umbilical cord, muscle, brain, liver spinal cord blood, blood or skin.

In a second object the present invention presents a pharmaceutical composition comprising the cells produced according to the method of the present invention, wherein the cells express at least one of the markers selected from the group consisting of p75NTR, αSMA, COL1α1, DESMIN, PDGFRβ, NCAM, NGF, and VIMENTIN. In a preferred embodiment, said cells express all of the markers DESMIN, PDGFRβ, NCAM, NGF and VIMENTIN. In a more preferred embodiment said cells express all of the markers p75NTR, αSMA, COL1α1, DESMIN, PDGFRβ, NCAM, NGF and VIMENTIN. In an even more preferred embodiment, said cells additionally show fluorescence under UV light (UV$^+$).

In a preferred embodiment, said pharmaceutical composition comprises cells produced according to the method of the present invention, wherein the cells show fluorescence under UV light (UV$^+$).

In another preferred embodiment, said pharmaceutical composition is for use in treatment of a subject with a liver deficiency, wherein said treatment comprises administering a therapeutically effective amount of the cells produced according to the method of the present invention to said subject. In a more preferred embodiment, said subject is a human.

Typically, said pharmaceutical composition may additional comprise a pharmaceutically acceptable carrier.

Typically, said cells produced according to the method of the present invention are also useful, among other applications, for liver metabolism studies, liver toxicity studies, fibrogenic studies, or to support hepatocyte function in co-culture setting.

Such co-cultures could for example comprise hepatocyte-like cells and hepatic stellate cells. Hence, the present invention also provides a co-culture of hepatocyte-like cells and hepatic stellate cells wherein said hepatic stellate cells are obtained using the method of the current invention; i.e. using the following method:
(a) culturing pluripotent cells with about 1 ng/ml to about 200 ng/ml BM P4;
(b) then culturing the cells of step (a) with about 1 ng/ml to about 200 ng/ml FGF1 and about 1 ng/ml to about 200 ng/ml FGF3;
(c) then culturing the cells of step (b) with about 0.5 μM to about 50 μM retinol and about 10 μM to about 1 mM palmitic acid; and
(d) isolating hepatic stellate cells produced by the differentiation protocol.

In a specific embodiment, said co-cultures are 3D co-cultures of hepatocyte-like cells and hepatic stellate cells; wherein said hepatic stellate cells are obtained using the method of the current invention.

In an even further embodiment, in said 3D co-cultures of hepatocyte-like cells and hepatic stellate cells; said hepatic stellate cells obtained using the method of the current invention are present in equal or excess amounts of said hepatocyte-like cells.

In a further embodiment of said (3D) co-cultures, said hepatocyte-like cells are derived from human induced pluripotent stem cells and said hepatic stellate cells are hiPSC derived hepatic stellate cells obtained using the method of the current invention.

In yet a further embodiment of said (3D) co-cultures, said hepatocyte-like cells are HepaRG cells and said hepatic stellate cells are hiPSC derived hepatic stellate cells obtained using the method of the current invention. A 3D co-culture according to this embodiment is provided in example 5 as provided herein after.

In another embodiment, said hepatic stellate cells obtained using the method of the current invention, are useful, among other applications, in particular when co-cultured as described hereinabove with hepatocyte-like cells, in 2D and 3D co-cultures, for liver toxicity studies and fibrogenic studies, including screening assays to identify (non-) toxic and (non-) fibrogenic compounds.

Uses for the Cells (1) Therapy of Liver Failure:

The invention is directed to methods of treating liver deficiencies by administering the cells of the invention to a subject with the liver deficiency. Such deficiencies include, but are not limited to, toxic liver disease, metabolic liver disease, acute liver necrosis, effects of acetaminophen, hemochromatosis, Wilson's Disease, Crigler Najar, hereditary tyrosinemia, familial intrahepatic cholestatis type 3, ornithine transcarbamylase (OTC) deficiency, and urea cycle disorder.

Further diseases include, but are not limited to viral hepatitis, chronic viral hepatitis A, B, C, acute hepatitis A, B, C, D, E, cytomegalovirus and herpes simplex virus; liver dysfunction in other infectious diseases such as, without limitation, toxoplasmosis, hepatosplenic schistosomiasis, liver disease in syphilis, leptospirosis and amoebiasis; metabolic diseases such as, without limitation, haemochromatosis, Gilbert's syndrome, Dubin-Johnson syndrome and Rotor's syndrome; alcoholic liver disease such as, without limitation, fatty liver, fibrosis, sclerosis and cirrhosis; and toxic liver disease.

(2) Bioartificial Liver (BAL) Devices

In patients with terminal liver failure, the use of bioartificial liver devices has been proposed to bridge the time to liver transplantation. BAL devices are designed to support the detoxification functions performed by the liver, hence decreasing the risk and severity of CNS complications associated with acute liver failure. BAL devices could benefit three groups of patients; those with fulminant hepatic failure, those waiting for an imminent transplant, and those with early failure of a liver transplant. Although some positive results have been seen in patients with liver failure, further exploration of the usefulness of BAL devices has been hampered by lack of suitable cells. Currently, tumor-derived cell lines or animal cells, which might be associated with possible tumor cell seeding, immune responses, and xeno-zoonoses, are used. The availability of cells with full mature hepatic function of human origin, would enable investigators to further test and optimize BAL devices to bridge patients till the liver spontaneously regenerates or a donor-liver is available. Although clinical trials have in general not been successful, some encouraging results have been seen in patients with acute liver failure. Accordingly, the cells of the invention can be used in such bioartificial liver devices.

(3) Pharmaceutical Testing, e.g. Toxicity Screens

As discussed in the background of this application, the quiescent hepatic stellate cells are the chief cells responsible for liver fibrosis. A renewable source of these cells, therefore, is highly desirable for discovering compounds that may be effective in an anti-fibrotic therapy. The antifibrotic therapies must be inhibiting the activation of the hepatic stellate cells. This is responsible for the fibrotic response to injury. Accordingly, the quiescent hepatic stellate cells produced by the methods described in this application can be used to screen for compounds that inhibit/prevent stellate cell activation and, therefore, are potential candidates for treatment and prevention of liver fibrosis. For example, in such screening assays HSC activation markers, e.g. ACTA2, Col1a1, Col3a1, Timp1, TGFbeta, Lox and/or Loxl1/2, may be used as a read-out for hepatocyte toxicity and potential fibrogenesis induction, whereby more specifically the increase of HSC activation markers (e.g. ACTA2, Col1a1, Col3a1, Timp1, TGFbeta, Lox and/or Loxl1/2) is indicative of hepatocyte toxicity and potential fibrogenesis induction, and whereby a decrease of these HSC activation markers (e.g. ACTA2, Col1a1, Col3a1, Timp1, TGFbeta, Lox and/or Loxl1/2) is indicative of a non-toxic and/or an anti-fibrotic compound.

Drug discovery involves screening one or more compounds for the ability to modulate the function or phenotype of the HSCs. Accordingly, the assay may be designed to be conducted in vivo or in vitro.

One could directly assay protein or RNA. This can be done through any of the well-known techniques available in the art, such as by FACS and other antibody-based detection methods and PCR and other hybridization-based detection methods. One could also perform biological assays for one or more biological effects of the agent to be tested.

Assays for expression/secretion include, but are not limited to, ELISA, Luminex. qRTPCR, anti-factor western blots, and factor immunohistochemistry.

Agents can be discovered through screening the cells with large combinatorial libraries. These compound libraries may be libraries of agents that include, but are not limited to, small organic molecules, antisense nucleic acids, siRNA DNA aptamers, peptides, antibodies, non-antibody proteins, cytokines, chemokines, and chemo-attractants.

The present invention is additionally described by way of the following illustrative, non-limiting Examples that provides a better understanding of the present invention and of its many advantages.

EXAMPLES

Material and Methods

Pluripotent stem cells (PSC) expansion. Prior to starting the hepatic stellate cells (HSC) differentiation, undifferentiated iPS cells are expanded on vitronectin (Life Technologies, California) coated plates and cultured with Essential 8™ Medium consisting of DEMEM/F-12 1:1 and Essential 8™ Supplement (50x) (Life Technologies).

Embryonic stem cells were expanded as previously described in (2).

HSC Differentiation. To start the HSC differentiation protocol, human PSC cells were plated in 12 well plates (TPP) coated with Matrigel-Matrix Growth factor reduced (VWR) diluted with DMEM low glucose (Life Technologies) for 1 hour at 37° C. or at 4° C. overnight. First, cells are detached from vitronectin coated plates by adding Trypsin (0.05%) (Biological Industries) and incubated at 37° C. until the edges of the colonies start to detach (usually around 5 minutes). Then, single PSC cells were seeded at approximately 350.000 cells/well and cultured in E8™ medium. HSC differentiation is started when the cells reach 50% of confluence, usually after 2-3 days. HSC Differentiation Medium consist of 57% DMEM, low glucose (Gibco), 40% MCDB-201-water (Sigma), 0.25× linoleic acid-bovine serum albumin (Sigma), 0.25× insulin-transferrin-selenium (Sigma), 1% penicillin streptomycin (Lonza), $10^{-4}$M L-ascorbic acid (Sigma), 2.5 µM dexamethasone (Sigma) and 50 µM 2-mercaptoethanol (Invitrogene). Plates were kept at 5% $CO_2$ in an incubator during the differentiation procedure. Medium was changed every 48 hours. Cytokines (RaD) were added in the medium as follows: bone morphogenetic protein (BMP) 4 (20 ng/ml) from day 0 to day 4, fibroblast growth factor (FGF) 1 and 3 (20 ng/ml) from day 4 to day 6. Moreover, retinol (5 µM) and palmitic acid (100 µM) (both, Sigma) were added from day 6 to day 12. The differentiation leads to subsequently intermediate populations mimicking fetal liver development such as multipotent mesoderm population ($NCAM^+$, $KDR^+$), liver mesenchymal cells ($PDGFR\alpha^+$, $CD73^+$), mesothelial cells ($DESMIN^+$, $P75NTR^+$, $ALCAM^+$) and fetal HSC ($DESMIN^+$, $P75NTR^+$, $ALCAM^+$). A diagram of the differentiation protocol is found in FIG. 1.

PSC-derived HSC-like cells expansion. At the end of the differentiation, at day 12, Matrigel-Matrix was recovered by incubating differentiated cells with Cell recovery Solution (BD) for 30 minutes on ice. Differentiated cells were detached with trypsin (0.05%). Next, 250.000 differentiated cells were seeded on 12 well plates coated with Matrigel-Matrix Growth Factor Reduced (VWR) diluted with DMEM low glucose (Life Technologies) for 1 hour at 37° C. or at 4° C. overnight. iHSC Medium was based on, and slightly modified, HSC Differentiation Medium and it consists of changing DMEM low glucose by Glutamax (Life Technologies) and by adding 10% FBS (Life technologies), retinol (5 µM) and palmitic acid (100 µM) (both, Sigma). Medium was changed every 48 hours.

Gene expression analysis. RNA from sorted cells was obtained using the RNeasy Micro Kit (Qiagen). Total RNA was retrotranscribed using a high capacity complementary DNA reverse-transcription kit (Applied Biosystems, Foster City, Calif.). Gene expression was determined by quantitative real time PCR on an ABI 7900HT cycler (Applied Biosystems) using SYBR green master mix (Life technologies). Individual gene expression was normalized to GAPDH. Relative expression was calculated using the comparative Ct method ($2^{-\Delta\Delta Ct}$). Gene specific primers were produced by Integrated DNA Technologies (Leuven, Belgium).

Immunostaining. Cells were fixed using 10% Neutral Buffered Formalin for 15 min, permeabilized with 0.2% Triton X-100 in PBS (Sigma-Aldrich), and blocked with 3% serum. Cells were incubated overnight at 4° C. with the primary antibody or isotype antibody diluted with DAKO REAL™ Antibody diluent (DAKO Glostrup, Denmark). Secondary antibodies (1:500 dilution) were incubated for 30 min in order to ensure nuclear staining, samples were mounted with Mounting Medium for Fluorescence with 4',6-diamidino-2-phenylindole (DAPI) (Vector Laboratories, Burlingame, Calif.). Immunofluorescence staining was analyzed with a Nikon Eclypse E600.

PSC-derived HSC-like cells isolation from differentiated mixture. Differentiated cells at day 12 were detached with trypsin (0.05%) and suspended in 5% FBS, 2 mM EDTA buffer and incubated for 30 minutes at 4° C. with antibodies against PDGFRβ (PE mouse Anti-Human CD 140b, BD Pharmingen™) or with control isotype. PSC-derived HSC-like cells enriched population was sorted out through a positive selection for PDGFRβ expressing cells (PDGFRβ+) and for ultraviolet positivity, using fluorescence activated cell sorter (FACS-Aria BD Biosciences) (fluorescence under UV light or UV+). Purified PSC-derived HSC-like cells population was immediately used for mRNA extraction.

Transcriptomic analysis of PSC-derived HSC-like cells. A total of 12 mRNA samples, 3 freshly isolated iHSC, 3 HSC-like at passage 1, 3 iPS samples harvested from the differentiation plate at day 0 and finally, 3 parental BJ1 samples were analyzed for gene expression profiling using Affymetrix HG-U219 genechips (Affymetrix, Santa Clara, Calif., USA). Transcriptomic profiles were analyzed together with previously published expression data generated from human quiescent HSC (n=7), their respective activated HSC samples (n=7) and three human hepatocyte samples (n=3) (3, 4).

Functional analysis of PSC-derived HSC-like cells. At day 12, differentiated mixture containing approximately 70% of PDGFRβ cells, was incubated with transforming growth factor β (TGFβ) 5 ng/mL, lipopolysaccharide (LPS) 1 µg/mL or FBS (10%). Changes in Pro-inflammatory and pro-fibrogenic genes were evaluated by qPCR after 24 hours of incubation.

3D culture of PSC-derived HSC-like cells with human hepatocytes. iPS-derived HSC-like cells and human hepatocytes were cultured in a 3D configuration in a ratio of 1:1. 3D-aggregates were generated by seeding 25 µL hanging drops containing 10,000 cells. After three days, formed spheroids were cultured in suspension using non-adherent plates coated with poly-(2-hydroxyethyl methacrylate) (Sigma-Aldrich).

Vitamin A storage capability of PSC-derived HSC-like cells. Vitamin A intensity of iPSC-derived HSC-like cells was indirectly determined by measuring the auto-fluorescence after UV light excitation (retinyl esters auto-fluorescence at 328 nm) using a FACS-Aria (BD Biosciences). Percentage of the decrease in vitamin A intensity was evaluated in PSC-derived HSC-like cells before and after the regular medium was changed for a retinol free medium.

Example 1

Figure 1:
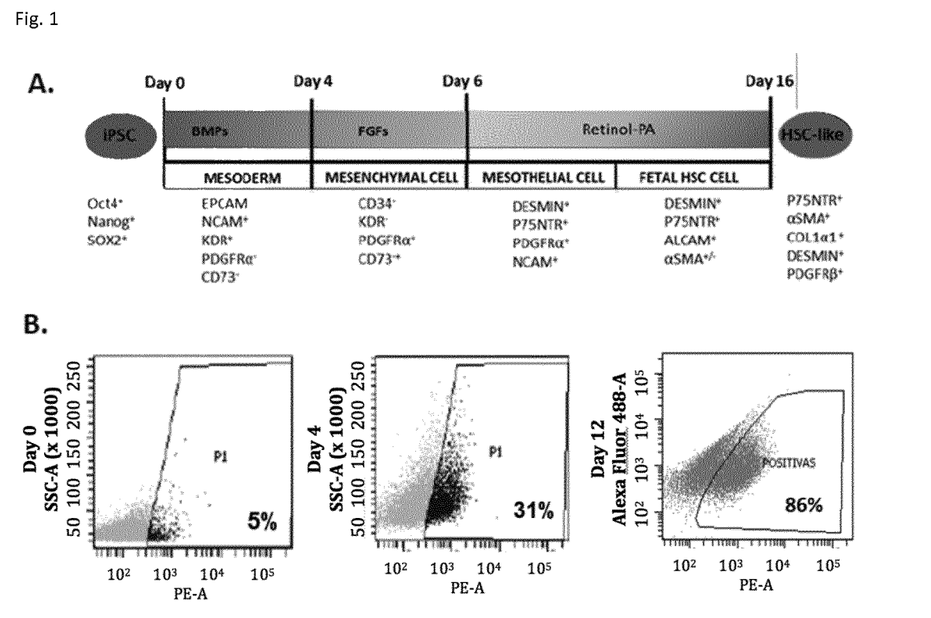
FIG. 1. Generation of human hepatic stellate-like cells from human iPSC. A. Schematic representation of the differentiation protocol. B. Representative flow cytometry profile showing the average number of PDGFRβ positive cells at different time points of the differentiation.

Differentiation of Pluripotent Stem Cells to Hepatic Stellate Cell-Like Cells and Characterization Pluripotent stem cells (PSC) have an inner cell mass phenotype, and therefore require to be directed along the embryonic and fetal development to acquire a mature hepatic stellate cell (HSC) phenotype. The protocol induces the specification to mesodermal cells, followed by the acquisition of a mesenchymal phenotype, mesothelial and finally the HSC phenotype (FIG. 1). A diagram of the differentiation protocol is found in FIG. 1A. One of the best-described extracellular markers in HSC is PDGFRβ. Therefore, we assessed the number on PSC-derived HSC-like cells by evaluating the percentage of cells expressing this receptor. As shown in FIG. 1B, flow cytometry analysis showed that along differentiation, the percentage of PDGFRβ cells increased, reaching a maximum of about 80% at day 12, suggesting that the majority of the differentiated cells have already acquired HSC phenotype. Moreover, PDGFRβ was also used to sort PSC-derived HSC-like cells by flow cytometry and analyze their phenotype by transcriptomic analysis.

Figure 2:
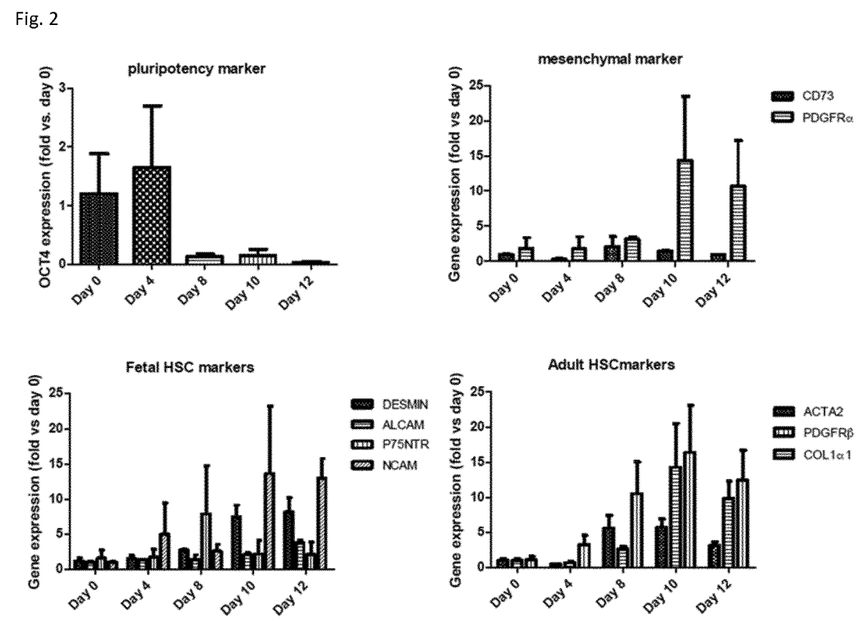
FIG. 2. Gene expression of pluripotency, liver mesenchymal, immature and mature HSC markers along iPS differentiation towards HSC-like population. mRNA expression was determined by quantitative PCR and expressed as fold versus day 0.

Incubation of undifferentiated PSC with bone morphogenetic protein 4 (BMP4) for 4 days induced a mesodermal phenotype, with the transient expression of kinase insert domain receptor (KDR), neural cell adhesion molecule (NCAM) and plateled-derived growth factor receptor (PDGFR) alpha. Following this step, cells were incubated with fibroblast growth factor (FGF) FGF1 and FGF3 together with retinol and palmitic acid to induce a mesenchymal phenotype. This procedure induced the expression of PDGFRα, CD73 but not KDR. HSC markers such as desmin, nerve growth factor receptor (P75NTR), activated leukocyte cell adhesion molecule (ALCAM), actin alpha 2 smooth muscle (ACTA2), Collagen (COL1α1) and PDGFRβ started to be expressed at day 8 with continuous incubation with retinol and palmitic acid and increased until the end of the differentiation (FIG. 2).

Figure 3:
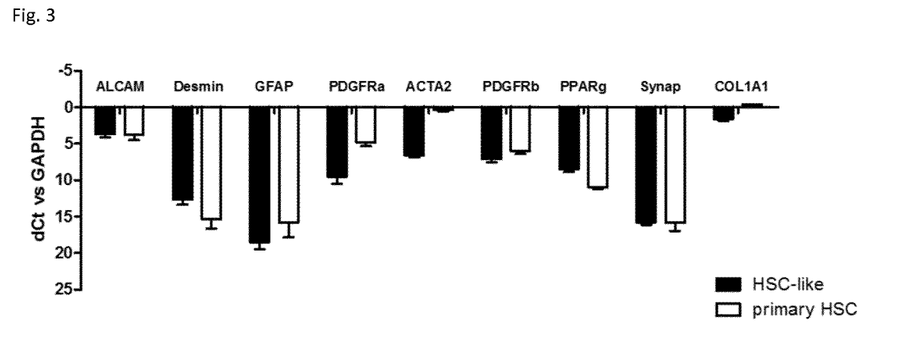
FIG. 3. iPSC-derived HSC characterization. Gene expression of adult HSC markers in iPS cell progeny and human primary HSC. Gene expression is expressed in dCT values.

The protocol induced the expression of well-known HSC markers also at gene and protein level. Immunostaining showed that human iPSC-differentiated HSC-like cells expressed ACTA2, VIMENTIN, PDGFRβ, NGF and NCAM at a comparable protein level to primary human HSC (data not shown). Moreover, cellular distribution of the different markers is equivalent as in primary cells. Quantitative analysis of HSC markers by real time PCR in differentiated HSC-like cells showed similar level of gene expression of HSC markers such as ALCAM, Desmin, glial fibrillary acidic protein (GFAP), PDGFRα, PDGFRβ, peroxisome proliferator-activated receptor (PPAR)γ, synaptophysin than primary HSC (FIG. 3). Interestingly, markers associated with HSC activation such as ACTA2 and COL1α1, where expressed at a lower level in differentiated HSC-like cells, suggesting that their level of activation may be lower and could better resemble an intermediate activated phenotype with more quiescent cell features.

Example 2

Culture of PSC-Derived HSC-Like Cells

Figure 4:
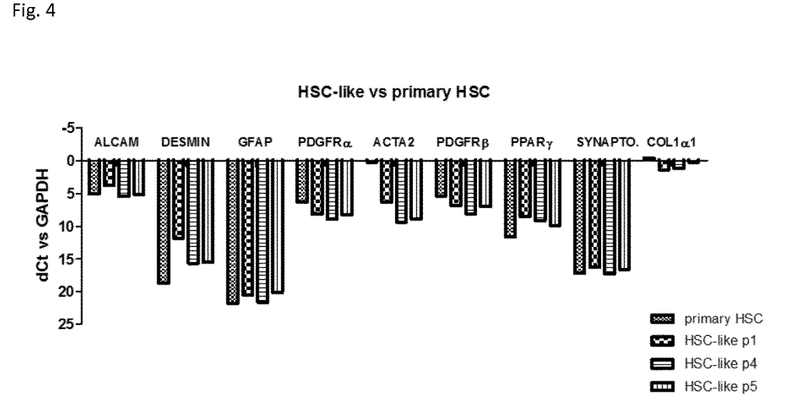
FIG. 4. iPSC-derived HSC stability in culture. Gene expression of adult markers in iPS cell progeny in subsequent passages. Gene expression is expressed in dCT values.

The number of cells from which to start the differentiation is not a concern, since PSC are a renewable source of stem cells and can be expanded almost indefinitely. Therefore, the differentiation could be scaled-up to obtain the desired number of PSC-derived HSC-like cells. However, the differentiation is expensive and for some applications it may be desirable to have the possibility to expand the PSC-derived HSC-like cells. In order to expand and subculture HSC-like cells, we have adapted the culture conditions for primary HSC. PSC-derived HSC-like cells could be expanded for several passages in culture while maintaining the phenotype of differentiated HSC-like cells. Moreover, PSC-derived HSC-like cells showed a phenotype similar to primary HSC, which was preserved upon sub-culture (FIG. 4).

Example 3

Transcriptomic Analysis of PSC-Derived HSC-Like Cells

Figure 5:
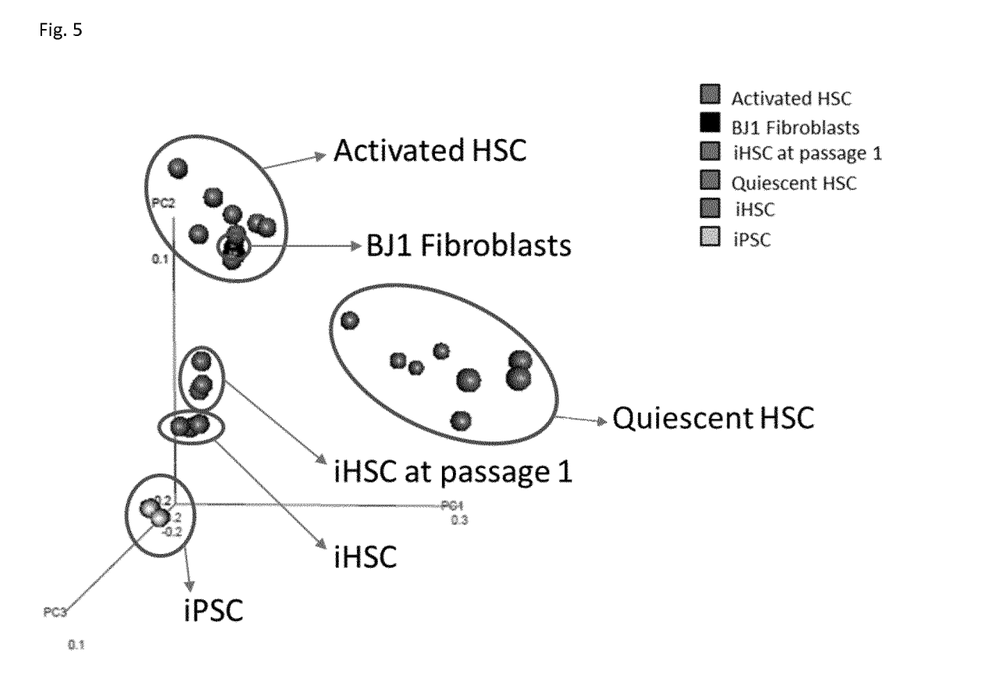
FIG. 5. Transcriptomic analysis of iPSC-derived HSC. 3D Principal Component Analysis (PCA) showing distances between the transcriptomic profiles of different human cell types. Human samples are placed in a three-dimensional space according to their transcriptomic signature. Represented human cell types are: activated HSC are represented (n=7), iPSC-derived HSC (n=3), cultured iPSC-derived HSC (passage one) (n=3), iPSC cells (n=3) and parental fibroblast BJ1 (n=3).

In order to further characterize PSC-derived HSC-like cells, a transcriptomic analysis was performed with differentiated cells and PSC-derived HSC-like cells at passage 1, and results were compared to parental undifferentiated PSC and primary quiescent and activated HSC. As shown in FIG. 5, principal component analysis, showed a clear clustering of each group of cells. Moreover, PSC-derived HSC-like cells showed an intermediate phenotype between quiescent and activated HSCs. Interestingly, PSC-derived HSC-like cells at passage 1, showed a closer identity to cultured activated HSC, suggesting that this expression profile could be due to culture conditions. Hierarchical cluster analysis of uncultured quiescent HSC and PSC-derived HSC-like cells showed a clear clustering of groups, showing that PSC-derived HSC-like cells still show differences in gene expression to quiescent HSC (data not shown). These differences may be related to an incomplete differentiation or to the culture effect, since quiescent HSC were analyzed directly after isolation from human liver tissue.

Example 4

Functional Analysis of PSC-Derived HSC-Like Cells

Figure 6:
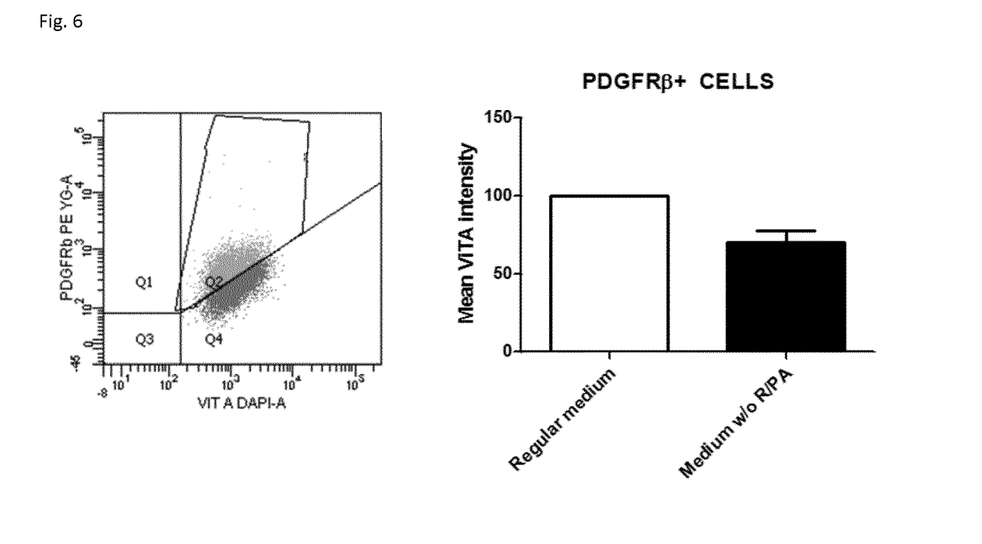
FIG. 6. Vitamin A storage capability of iPSC-derived HSC. Vitamin A intensity of iPSC-derived HSC cultured in a regular medium or cultured in a retinol and palmitic acid (PA) free medium. Left panel shows FACS analysis of iPSC-derived HSC cultured in regular medium, highlighting PDGFR$^+$ UV$^+$ (Vitamin A) double-positive cells. Results are shown as a decrease in the percentage of mean vitamin A intensity (right panel).

The main role of HSC in the liver is to metabolize retinol and store vitamin A and to be able to respond to injury and to activate and participate in the resolution of liver injury. Therefore, we assessed the capability of PSC-derived HSC-like cells to store retinol in lipid droplets and to respond to pro-fibrogenic and pro-inflammatory mediators. As shown in FIG. 6, incubation of PSC-derived HSC-like cells with retinol and palmitic acid (regular medium) increased the level of auto-fluorescence under ultraviolet spectrum, a well-known method to evaluate the content of vitamin A in lipid droplets. Moreover, the incubation of differentiated cells without retinol and palmitic acid reduced the auto-fluorescence level in the cells, suggesting the reduction of vitamin A content. As negative control a cell line of macrophages was used, indicating that this capacity could be restricted to HSC-like cells (data not shown).

Figure 7:
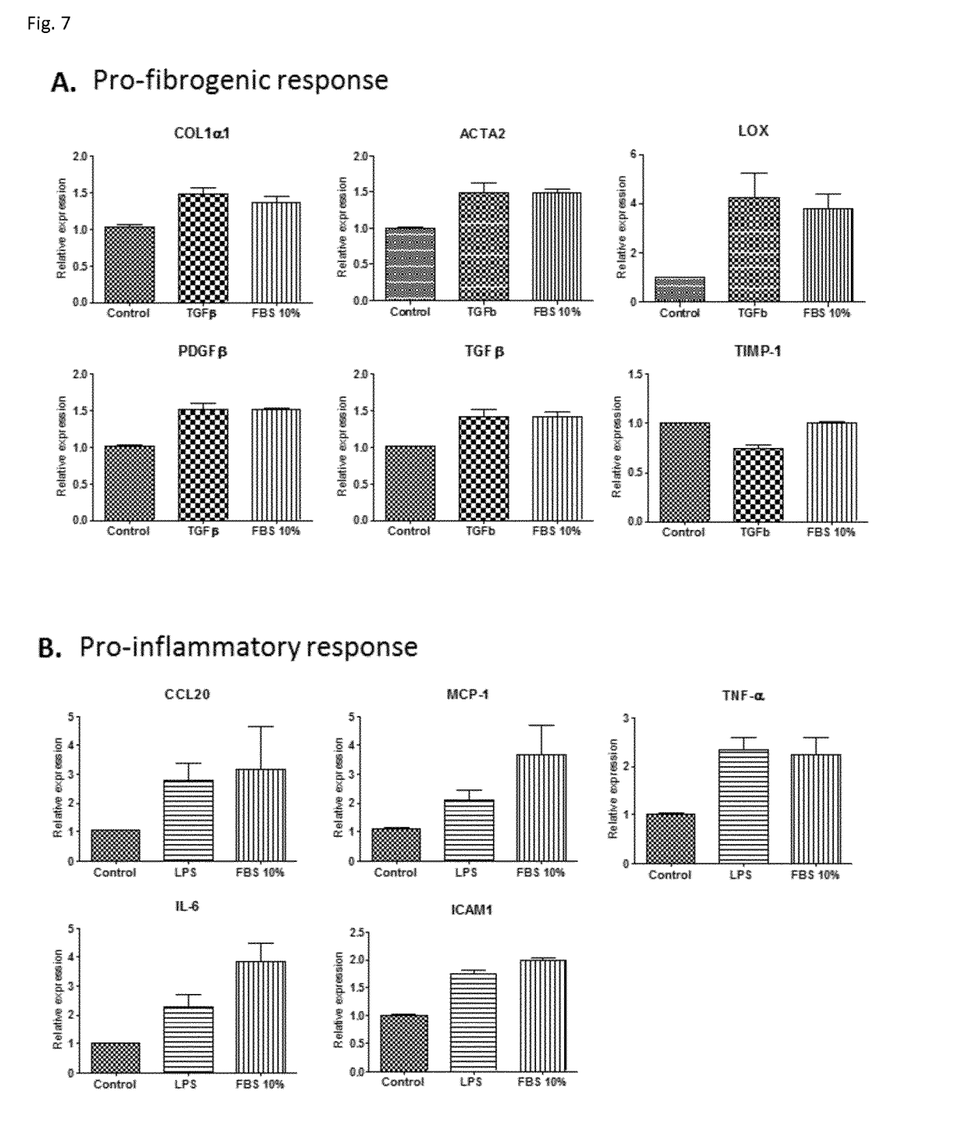
FIG. 7. Functional characterization of iPSC-derived HSC. Pro-fibrogenic (A) and pro-inflammatory (B) response of iPS cells progeny. HSC-like cells were incubated with transforming growth factor β (TGFβ) 5 ng/ml, lipopolysaccharide (LPS) 1 µg/ml and FBS (10%) for 24 hours. mRNA expression was determined by quantitative real time PCR and was expressed as fold versus control (medium without FBS).

In order to evaluate the capacity of PSC-derived HSC-like cells to respond to injury, differentiated cells were treated with transforming growth factor (TGF)β, lipopolysaccharide (LPS) and fetal calf serum (well-known inducer of HSC activation). As shown in FIG. 7, PSC-derived HSC-like cells showed a clear respond to fibrogenic and inflammatory mediators, up-regulating activation markers such as COL1α1, Acta2, lysyl oxidase (LOX) or TGFβ, and inflammatory markers such as chemokine (C-C motif) ligand 20 (CCL20), monocyte chemoattractant protein 1 (MCP-1), tumour necrosis factor (TNF)-α, Interleukin 6 (IL-6), and intercellular adhesion molecule (ICAM)1. These results suggest that PSC-derived HSC-like cells are able to respond to injury mediators, to further activate and promote the inflammatory response to injury.

Example 5

3D Culture of PSC-Derived HSC-Like Cells

Figure 8:
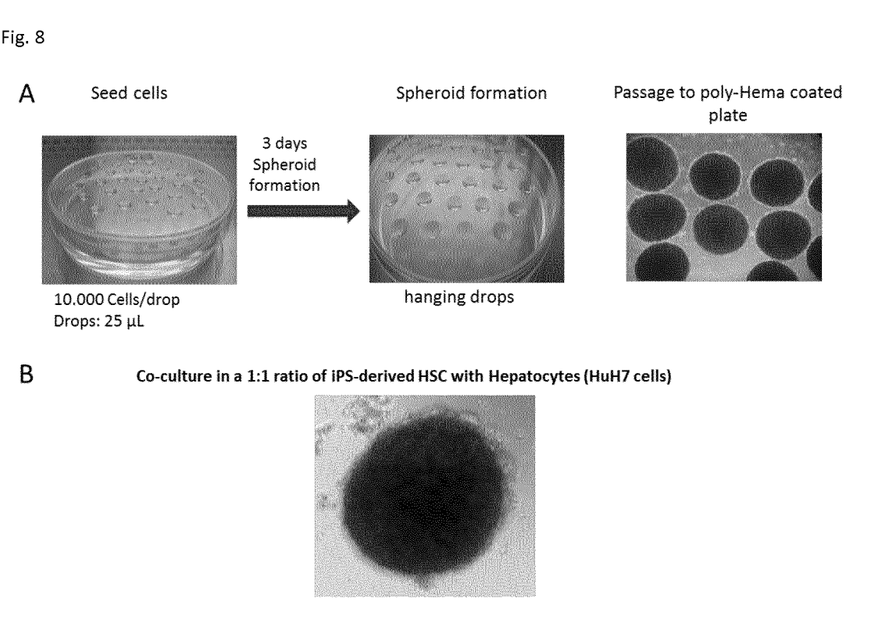
FIG. 8. Co-culture of iPS-derived HSC with hepatocytes. (A) iPS-derived HSC and huh7 cells were seeded 1:1 in hanging drops for 3 days to allow spheroid formation. Spheroids were then cultured in non-adherent plates. (B) Magnification picture of iPS-derived HSC and huh7 spheroid.

HSC are stromal cells of the liver, and therefore might be useful as supportive cells in long-term in in vitro studies with hepatocytes. PSC-derived HSC-like cells together with hepatocytes aggregated forming three-dimensional spheroids (FIG. 8). Generated spheroids can be maintained in culture for several days and could be used for toxicity and fibrogenic assays.

REFERENCES (1) Sancho-Bru P, Roelandt P, Narain N, Pauwelyn K, Notelaers T, Shimizu T, Ott M, Verfaillie C. Directed differentiation of murine-induced pluripotent stem cells to functional hepatocyte-like cells. J. Hepatol. 2011; 54(1): 98-107.

(2) Park Y, Chen Y, Ordovas L, Verfaillie CM. Hepatic differentiation of human embryonic stem cells on microcarriers. J Biotechnol. 2014; 174: 39-48.

(3) Coll M, El Taghdouini A, Perea L, Mannaerts I, Vila-Casadesús M, Blaya D, Rodrigo-Torres D, Affò S, Morales-Ibanez O, Graupera I, Lozano J J, Najimi M, Sokal E, Lambrecht J, Ginès P, van Grunsven L A, Sancho-Bru P. Integrative miRNA and Gene Expression Profiling Analysis of Human Quiescent Hepatic Stellate Cells. Sci Rep. 2015; 5: 11549.

(4) El Taghdouini A, Sørensen A L, Reiner A H, Coll M, Verhulst S, Mannaerts I, Øie C I, Smedsrød B, Najimi M, Sokal E, Luttun A, Sancho-Bru P, Collas P, van Grunsven L A. Genome-wide analysis of DNA methylation and gene expression patterns in purified, uncultured human liver cells and activated hepatic stellate cells. Oncotarget 2015; 6(29): 26729-45.

The invention claimed is:

1. A method for producing cells with a hepatic stellate cell phenotype, the method comprising:
(a) culturing pluripotent stem cells with from 1 ng/ml to 200 ng/ml bone morphogenetic protein 4 (BMP4);
(b) culturing the cells obtained from step (a) with from 1 ng/ml to 200 ng/ml fibroblast growth factor 1 (FGF1) and from 1 ng/ml to 200 ng/ml fibroblast growth factor 3 (FGF3);
(c) culturing the cells obtained from step (b) with from 0.5μM to 50μM retinol and from 10μM to 1 mM palmitic acid, thereby obtaining cells with a hepatic stellate cell phenotype; and
(d) isolating the cells with a hepatic stellate cell phenotype,
wherein the pluripotent stem cells are selected from the group consisting of mouse pluripotent stem cells, human pluripotent stem cells, rat pluripotent stem cells, and induced pluripotent stem cells (iPSC).

2. The method according to claim 1, wherein step (a) comprises culturing the pluripotent stem cells with about 10 ng/ml BMP4.

3. The method according to claim 1, wherein step (b) comprises culturing the cells obtained from step (a) with 20 ng/ml FGF1 and 20 ng/ml FGF3.

4. The method according to claim 1, wherein step (c) comprises culturing the cells obtained from step (b) with 5μM retinol and 100μM palmitic acid.

5. The method according to claim 1, wherein:
step (a) comprises culturing the pluripotent cells with 20 ng/ml BMP4;
step (b) comprises culturing the cells obtained in step (a) with 20 ng/ml FGF1 and 20 ng/ml FGF3; and
step (c) comprises culturing the cells obtained in step (b) with 5μM retinol and 100μM palmitic acid.

6. The method according to claim 1, wherein the culturing of each of steps (a), (b), and (c) is performed for at least two days.

7. The method according to claim 1, wherein the culturing of step (a) is performed for about 4 days, the culturing of step (b) is performed for about two days, and the culturing of step (c) is performed for about six days.

8. The method according to claim 1, wherein the pluripotent stem cells are iPSC.

9. The method according to claim 1, wherein the iPSC are derived from bone marrow, placenta, umbilical cord, muscle, brain, liver spinal cord blood, blood or skin.

10. The method according to claim 1, wherein the isolation of cells with a hepatic stellate cell phenotype of step (d) is carried out by positive selection for nerve growth factor receptor (p75NTR) and platelet-derived growth factor receptor b (PDGFRb), and/or for fluorescence under UV light (UV+).

11. The method according to claim 1, wherein the isolation of cells with a hepatic stellate cell phenotype of step (d) is carried out by positive selection for the marker PDGFRb.

* * * * *